(12) United States Patent
Kanemitsu et al.

(10) Patent No.: US 7,756,245 B2
(45) Date of Patent: Jul. 13, 2010

(54) MAMMOGRAPHY APPARATUS

(75) Inventors: Shingo Kanemitsu, Nasushiobara (JP); Rina Takahashi, Funabashi (JP); Makiko Itaya, Tokyo (JP); Naoko Kuratomi, Sakura (JP); Noriaki Baba, Tokyo (JP); Kenji Ido, Yokohama (JP); Yuko Saito, Tachikawa (JP); Naoko Chikuma, Tokyo (JP); Masatsugu Kawamata, Utsunomiya (JP); Takehito Tomaru, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/968,454

(22) Filed: Jan. 2, 2008

(65) Prior Publication Data
US 2009/0003520 A1    Jan. 1, 2009

(30) Foreign Application Priority Data
Jan. 12, 2007    (JP) .............................. 2007-004916

(51) Int. Cl.
*A61B 6/04* (2006.01)

(52) U.S. Cl. ......................................... 378/37; 378/208
(58) Field of Classification Search .................. 378/20, 378/37, 177, 208
See application file for complete search history.

(56) References Cited

U.S. PATENT DOCUMENTS

2006/0115041 A1 *  6/2006  Roncaglioni et al. .......... 378/37

FOREIGN PATENT DOCUMENTS

CN    2750729    1/2006

* cited by examiner

*Primary Examiner*—Courtney Thomas
(74) *Attorney, Agent, or Firm*—Oblon, Spivak, McClelland, Maier & Neustadt, L.L.P

(57) ABSTRACT

A mammography apparatus includes a rotatably supported arm, an X-ray tube to generate X-rays, which is held on one end of the arm, an imaging stage which is held on the other end of the arm, an X-ray detector which detects the X-rays having passed through patient's breast and is contained in the imaging stage, and an armrest which has an armrest main body portion having a convexly curved surface, and a continuous base portion to fix the armrest main body on the arm.

12 Claims, 4 Drawing Sheets

MAMMOGRAPHY APPARATUS

CROSS-REFERENCE TO RELATED APPLICATIONS

This application is based upon and claims the benefit of priority from prior Japanese Patent Application No. 2007-004916, filed Jan. 12, 2007, the entire contents of which are incorporated herein by reference.

BACKGROUND OF THE INVENTION

1. Field of the Invention

The present invention relates to a mammography apparatus which performs imaging by an X-ray tube and an X-ray detector by compressing a breast with a compression paddle.

2. Description of the Related Art

Mammography apparatuses are radiographic apparatuses exclusively for breasts, which compress breasts placed on an imaging table by a compression paddle to spread out mammary gland, and obtain two-dimensional images. Mammary glands in breasts have a structure of branching out in a three-dimensional manner and connected to lobulus. Therefore, when breasts are imaged without compression, many mammary glands overlap each other, and accurate evaluation cannot be performed. Therefore, breasts are compressed to be thinned and spread out, thereby overlapping of mammary glands is reduced, and X-ray imaging by a lower dose is enabled.

In imaging by using a mammography apparatus, breast being an imaging object must be fixed with respect to the mammography apparatus together with the patient's body, as in other modality imaging methods. Therefore, conventional mammography apparatuses have a structure in which cylindrical grips (also referred to as handles) are fixed on seats in two or more positions in a column portion of a rotation arm, in a state of being slightly spaced from the arm. The patient steadily holds the grips in the above state by grasping the grips by the patient's fingers, and brings one's body close to the arm. Thereby, the patient can steadily fix one's body and breast with respect to the mammography apparatus.

However, when the patient holds the grips with strength in one's arms, the patient's arm muscles and pectoral muscles are strongly tensed, and there is caused a situation in which the patient's breast cannot be properly spread out. Further, there are cases where the patient's feels pain by compression, in the state where the patient's pectoral muscles or the like are strongly tensed.

BRIEF SUMMARY OF THE INVENTION

An object of the present invention is to provide a mammography apparatus which enables suitable fixing of patient's breast together with one's body, while preventing excessive tension of pectoral muscles and the like.

According to an aspect of the present invention, there is provided a mammography apparatus comprising: a rotatably supported arm; an X-ray tube to generate X-rays, which is held on one end of the arm; an imaging stage which is held on the other end of the arm; an X-ray detector to detect the X-rays which have passed through patient's breast, the X-ray detector being contained in the imaging stage; and an armrest which has an armrest main body portion having a convexly curved surface, and a continuous base portion to fix the armrest main body on the arm.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of a mammography apparatus according to the present invention is explained below with reference to drawings.

Figure 1:
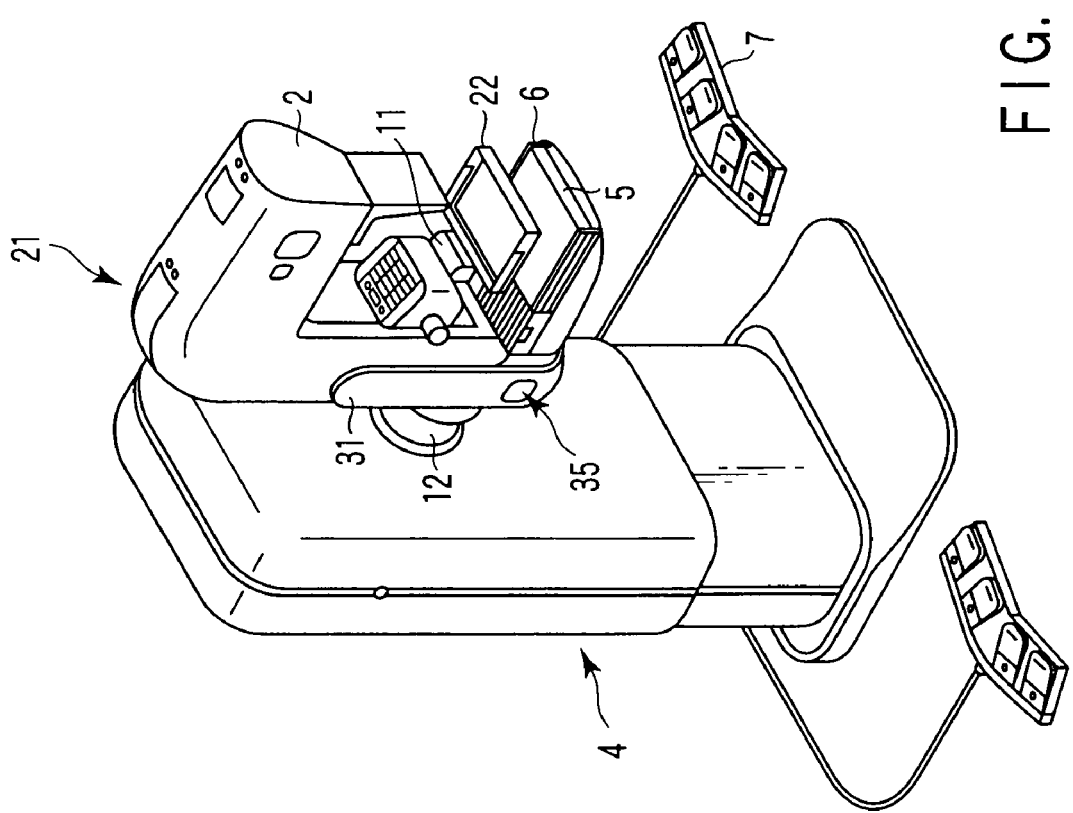
FIG. 1 is an external view of a mammography apparatus according to an embodiment of the present invention.

FIG. 1 illustrates an appearance of a mammography apparatus according to the embodiment. The mammography apparatus has a stand 4. The stand 4 rotatably supports an almost L-shaped or I-shaped arm 21 by a horizontal pillar 12, with a rotational axis R serving as a center. An X-ray tube 2 is provided on one end of the arm 21. Actually, the X-ray tube 2 is covered with a housing. A high-voltage generator 3 is contained in the stand 4. The high-voltage generator 3 applies high voltage (tube voltage) between electrodes of the X-ray tube 2, and supplies a filament current to a filament of the X-ray tube 2. Thereby, X-rays are generated in the X-ray tube 2.

An imaging stage 6 is provided on the other end of the arm 21. An X-ray detector 5 is contained in the imaging stage 6. A film cassette, a CR cassette, or plane X-ray detector (flat panel detector: FPD) is adopted as the X-ray detector 5. The X-ray detector 5 is provided in a direction of facing the X-ray tube 2, and detects X-rays which have passed through patient's compressed breast.

The arm 21 is provided with a compression mechanism 11. The compression mechanism 11 is formed of a compression paddle 22, a moving mechanism thereof, and a movement drive section. The compression paddle 22 moves in directions of approaching/going away from the imaging stage 6, while maintaining a state of being parallel with the imaging stage 6. The compression paddle 22 compresses the patient's breast with the imaging stage 6. Movement of the compression paddle 22 can be operated by the footswitch 7. Rotation of the arm 21 can be operated at hand by the radiologist by using operation buttons of an operation panel 35 provided in a part of the armrest 31.

Figure 2:
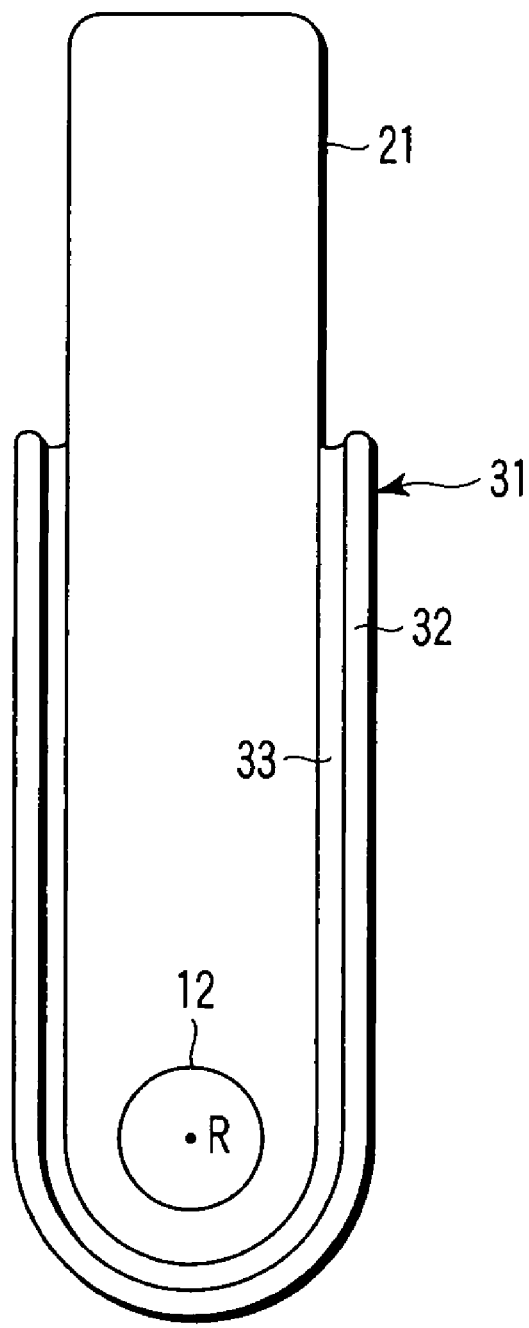
FIG. 2 is a diagram of an L-shaped arm and an armrest of FIG. 1, as viewed from the stand side.
Figure 3:
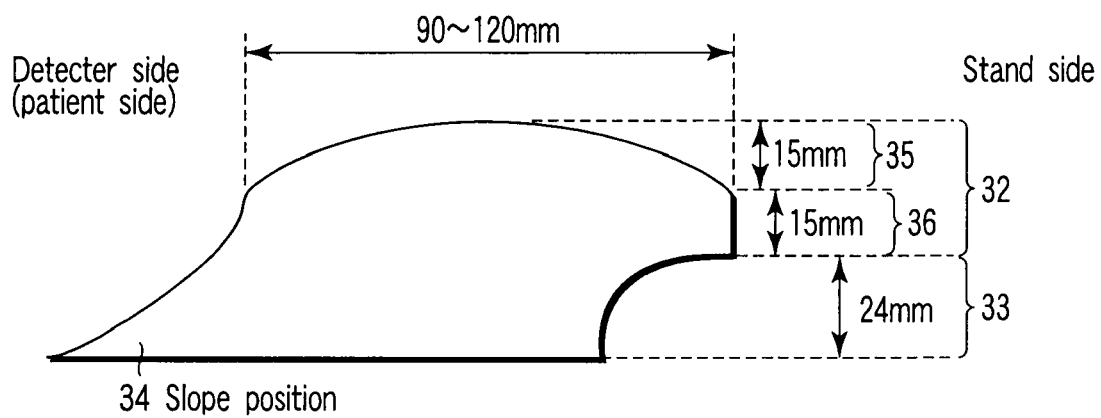
FIG. 3 is a horizontal cross-sectional view of the armrest of FIG. 1.
Figure 4:
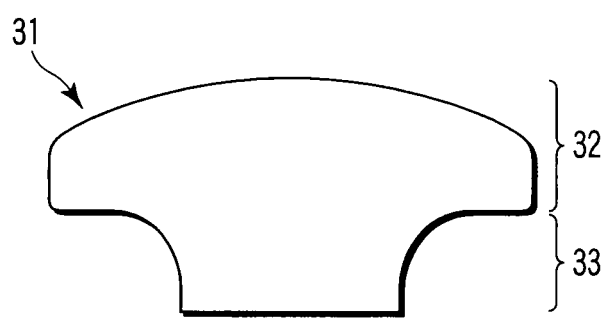
FIG. 4 is another horizontal cross-sectional view of the armrest of FIG. 1.

As illustrated in FIGS. 2 and 3, the armrest 31 has a U shape to surround the arm 21. The armrest 31 is formed of an armrest main body portion 32 which has an almost cambered shape and a convexly curved surface, and a continuous base portion 33 which fixes the armrest main body portion 32 on the arm 21. Specifically, the surface of the armrest main body portion 32 is curved with a radius selected from a range of 100 to 110 mm.

The base portion 33 has a length almost equal to that of the armrest main body portion 32, not to make a gap between the armrest main body portion 32 and the arm 21, and continuously supports the armrest main body portion 32. This is a first difference in structure between the base portion 33 and conventional bar-shaped handles (grips) which are disposed with a gap from the arm. This structure of not having a gap eliminates the state where the patient holds the handles by grasping the handle with one's five fingers, and naturally generates a state where the patient hooks one's fingers on the armrest. This state can be further secured by the following many elements.

As illustrated in FIG. 3, the armrest main body portion 32 has a width of at least 90 mm. The armrest main body portion 32 has a width selected from a range of 90 to 120 mm. Typically, the armrest main body portion 32 has a width of 110 mm. This relatively large width increases its functionality as an armrest, and eliminates the state where the patient tightly grips the armrest by opposing one's thumb and forefinger, since the width is longer than the general length between the second joint of the forefinger and the first joint of the thumb of adults.

More specifically, as illustrated in FIG. 3, the armrest main body portion 32 is formed of a curved portion 35 having a thickness of at least 15 mm, and a flat portion 36 which supports the curved portion 35 and has a thickness of at least 15 mm. Actually, the curved portion 35 has a thickness selected from a range of 10 to 20 mm. The flat portion 36 has a thickness selected from a range of 10 to 20 mm.

The base portion 33 typically has a thickness of 24 mm. Actually, the base portion 33 has a thickness selected from a range of 20 to 30 mm, to prevent the patient's fingers from being caught. As illustrated in FIG. 3, the base portion 33 has a structure in which one side (the side distant from the patient) is recessed from the armrest main body portion 21, and the other side (the side close to the patient) is a slope portion 34 which spreads like a slope and has a width larger than that of the armrest main body portion 32. The base portion 33 may not have the slope portion 34, but may have a symmetrical shape in which both sides are recessed from the armrest main body portion 21. In this case, the base portion 33 has a width shorter than that of the armrest main body portion 32.

As described above, the armrest 31 is attached along the outer shape of the arm 21. The armrest 31 has a flat shape with respect to the shorter axis direction thereof, has a width enough to prevent the patient's thumb from reaching the back side of the armrest 31 when the patient lays one's hands on the armrest 31, and has the continuous base portion 33. In other words, the armrest 31 has a width in its shorter length direction, which is longer than a distance between the second joint of one's middle finger and the base of the thumb. Thereby, support of the patient can be achieved only by fingertips, without putting the thumb on the back side of the armrest 31. Therefore, it is possible to prevent tension of the patient's arm muscles and pectoral muscles caused by supporting oneself by griping the armrest 31 with the thumb put on the back side of the armrest 31. It is possible to stabilize the position of the patient oneself and resolve the patient's feelings of anxiety during imaging, while tension of arm muscles and pectoral muscles are prevented as much as possible, by action of hooking one's fingers on the armrest, instead of action of gripping the armrest.

Figure 5:
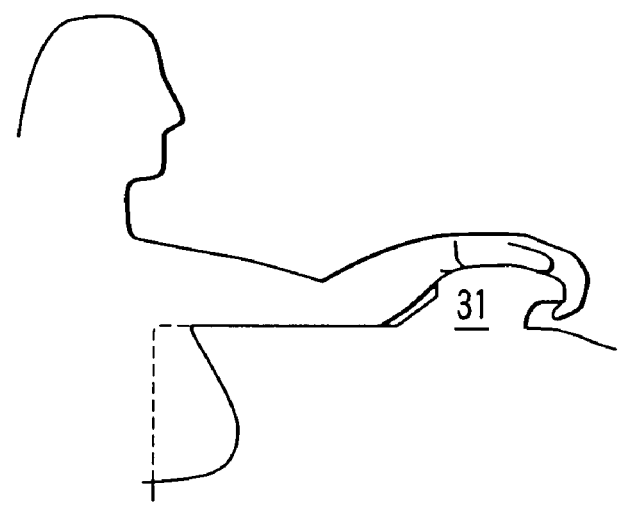
FIG. 5 is a horizontal cross-sectional view illustrating a state where the patient places one's arms on the armrest of FIG. 1 and hooks one's fingers on the armrest.
Figure 6:
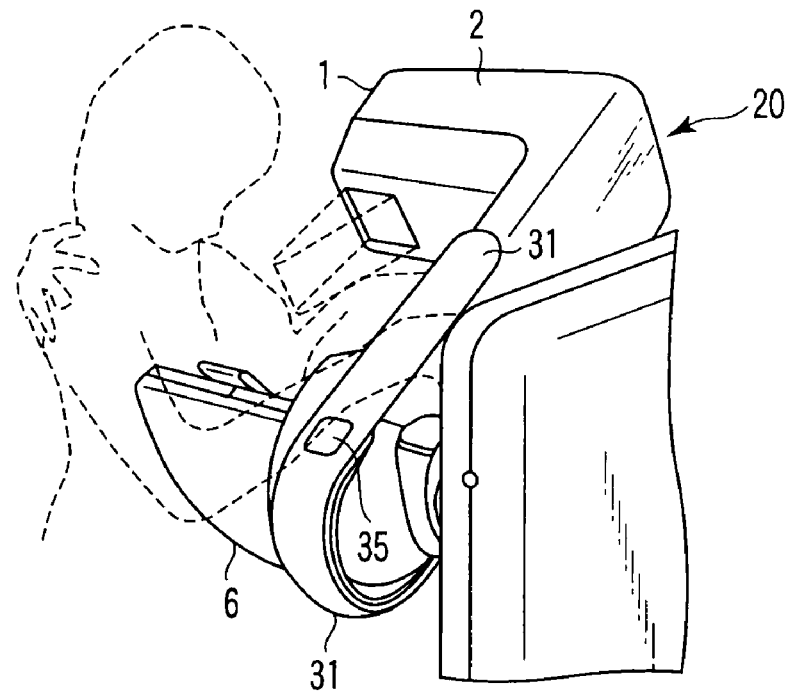
FIG. 6 is a perspective view illustrating a state where the patient places one's arms on the armrest of FIG. 1 and hooks one's fingers on the armrest.

FIGS. 5 and 6 illustrate such states of using the armrest 31. The patient's breast is held and compressed between the imaging stage 6 and the compression paddle 22. In that state, the patient places one's arms on the armrest 31, and hooks one's fingertips, typically the second joints of fingers, on an edge of the armrest main body portion 32 of the armrest 31. In that state, the patient bends one's arms to bring the chest close to the arm 21, and thereby fixes the patient's body with respect to the arm 21.

As described above, the patient cannot tightly grip the arm 21 by facing one's forefinger to one's thumb, unlike the prior art, and the patient fixes one's body with respect to the arm 21 in the state of hooking one's fingertips on the armrest main body portion 32. This prevents excessive tension of pectoral muscles and other muscles, and prevents the situation in which the patient's breast cannot be properly thinned out due to strong tension of pectoral muscles and the like. Further, it is possible to alleviate the patient's pain caused by compression.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mammography apparatus comprising:
    a rotatably supported arm;
    an X-ray tube to generate X-rays, which is held on one end of the arm;
    an imaging stage which is held on the other end of the arm;
    an X-ray detector to detect the X-rays which have passed through a patient's breast, the X-ray detector being contained in the imaging stage; and
    an armrest which has an armrest main body portion having a convexly curved surface, and a continuous base portion to fix the armrest main body on the arm, the armrest main body mounted along an outer shape of the arm.

2. A mammography apparatus according to claim 1, wherein
    the base portion has a length almost equal to length of the armrest main body portion, not to generate a gap between the armrest main body portion and the arm.

3. A mammography apparatus according to claim 1, wherein
    the armrest main body portion has a width of at least 90 mm.

4. A mammography apparatus according to claim 3, wherein
    the base portion has a width shorter than the width of the armrest main body portion.

5. A mammography apparatus according to claim 1, wherein
    the armrest main body portion has a thickness of at least 30 mm.

6. A mammography apparatus according to claim 1, wherein
    the base portion has a thickness of at least 24 mm.

7. A mammography apparatus according to claim 1, wherein
the convexly curved surface of the armrest main body portion has a radius selected from a range of 100 to 110 mm.

8. A mammography apparatus according to claim 1, wherein
both sides of the base portion are recessed from the armrest main body portion.

9. A mammography apparatus according to claim 1, wherein
the base portion has one side which is recessed from the armrest main body portion, and the other side which spreads like a slope.

10. A mammography apparatus according to claim 1, further comprising:
a compression mechanism which has a movable compression paddle to compress the patient's breast with the imaging stage; and
a foot switch to operate movement of the compression paddle;
an operator panel to operate movement of rotation of the arm, the operator panel being provided on a surface of the armrest.

11. A mammography apparatus comprising:
a rotatably supported arm;
an X-ray tube to generate X-rays, which is held on one end of the arm;
an imaging stage which is held on the other end of the arm;
an X-ray detector to detect the X-rays which have passed through a patient's breast, the X-ray detector being contained in the imaging stage; and
an armrest which is attached to the arm, and has a width of at least 90 mm and a convex surface, the armrest having an armrest main body mounted along an outer shape of the arm.

12. A mammography apparatus comprising:
a rotatably supported arm;
an X-ray tube to generate X-rays, which is held on one end of the arm;
an imaging stage which is held on the other end of the arm;
an X-ray detector to detect the X-rays which have passed through a patient's breast, the X-ray detector being contained in the imaging stage; and
an armrest which is provided along an outer shape of the arm and has a flat shape at a distal end of the armrest, the armrest having an armrest main body mounted along the outer shape of the arm.

* * * * *